United States Patent
Kobayashi et al.

(10) Patent No.: US 11,400,262 B2
(45) Date of Patent: Aug. 2, 2022

(54) GUIDEWIRE HAVING EXTERNAL COIL WITH SECTIONS OF DIFFERENT WINDING PITCHES AND RESIN COATINGS

(71) Applicant: ASAHI INTECC CO., LTD., Aichi (JP)

(72) Inventors: Hiroshi Kobayashi, Seto (JP); Tomomi Inoue, Seto (JP); Sho Kubota, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 204 days.

(21) Appl. No.: 16/783,181

(22) Filed: Feb. 6, 2020

(65) Prior Publication Data
US 2020/0171279 A1 Jun. 4, 2020

Related U.S. Application Data

(63) Continuation of application No. PCT/JP2017/035759, filed on Sep. 30, 2017.

(51) Int. Cl.
*A61M 25/09* (2006.01)

(52) U.S. Cl.
CPC ... *A61M 25/09* (2013.01); *A61M 2025/09083* (2013.01); *A61M 2205/0238* (2013.01); *A61M 2205/0266* (2013.01)

(58) Field of Classification Search
CPC ............ A61M 25/09; A61M 25/09016; A61M 25/09033; A61M 2025/09133; A61M 2025/09083; A61B 5/6851
See application file for complete search history.

(56) References Cited

U.S. PATENT DOCUMENTS

| | | | | |
|---|---|---|---|---|
| 5,259,393 | A * | 11/1993 | Corso, Jr | A61B 6/12 600/585 |
| 5,353,808 | A * | 10/1994 | Viera | A61M 25/09 600/434 |
| 5,376,083 | A * | 12/1994 | Mische | A61M 25/09 600/585 |
| 5,606,981 | A * | 3/1997 | Tartacower | A61M 25/09 600/585 |
| 5,925,016 | A * | 7/1999 | Chornenky | A61M 25/09 604/96.01 |
| 8,360,996 | B2 * | 1/2013 | Satou | A61M 25/09016 600/585 |
| 8,845,551 | B2 * | 9/2014 | Kato | A61M 25/09 600/585 |

(Continued)

FOREIGN PATENT DOCUMENTS

| | | | | |
|---|---|---|---|---|
| CN | 103354753 A | * | 10/2013 | ............ A61M 25/09 |
| CN | 104127950 A | * | 11/2014 | ............ A61M 25/09 |

(Continued)

*Primary Examiner* — Jason E Flick
*Assistant Examiner* — Adam J. Cermak
(74) *Attorney, Agent, or Firm* — Xsensus LLP

(57) ABSTRACT

A guide wire includes a core shaft, a coil wound around the core shaft, a distal-end joining region to which a distal end of the core shaft and a distal end of the coil are joined, and a proximal-end joining region to which a proximal end of the core shaft and a proximal end of the coil are joined, and the coil has a sparsely wound portion having a sparser coil pitch than other portions of the coil, the sparsely wound portion being disposed between the distal-end joining region and the proximal-end joining region.

5 Claims, 13 Drawing Sheets

(56) References Cited

U.S. PATENT DOCUMENTS

| | | | |
|---|---|---|---|
| 9,295,813 B2* | 3/2016 | Kanazawa | A61M 25/09 |
| 9,333,326 B2* | 5/2016 | Takada | A61M 25/09 |
| 9,522,256 B2* | 12/2016 | Takada | A61M 25/09 |
| 2004/0092845 A1* | 5/2004 | Gaber | A61M 25/09025 |
| | | | 600/585 |
| 2005/0177073 A1* | 8/2005 | Shiber | A61B 17/320758 |
| | | | 600/585 |
| 2005/0228431 A1* | 10/2005 | Meguro | A61M 29/02 |
| | | | 606/194 |
| 2006/0047224 A1* | 3/2006 | Grandfield | A61M 25/09 |
| | | | 600/585 |
| 2008/0004546 A1* | 1/2008 | Kato | A61M 25/09 |
| | | | 600/585 |
| 2008/0194992 A1* | 8/2008 | Satou | A61M 25/09 |
| | | | 600/585 |
| 2009/0299332 A1* | 12/2009 | Shireman | A61M 25/09 |
| | | | 604/526 |
| 2011/0015570 A1* | 1/2011 | Kato | A61L 31/022 |
| | | | 604/96.01 |
| 2011/0015618 A1 | 1/2011 | Satou et al. | |
| 2011/0245730 A1* | 10/2011 | Satozaki | A61L 31/10 |
| | | | 600/585 |
| 2012/0101408 A1* | 4/2012 | Patterson | A61M 25/09033 |
| | | | 600/585 |
| 2012/0220896 A1* | 8/2012 | Matsuo | A61M 25/09 |
| | | | 600/585 |
| 2012/0245488 A1* | 9/2012 | Matsumoto | A61M 25/09 |
| | | | 600/585 |
| 2012/0265100 A1* | 10/2012 | Maki | A61M 25/09 |
| | | | 600/585 |
| 2012/0323145 A1* | 12/2012 | Nagano | A61M 25/09 |
| | | | 600/585 |
| 2013/0006221 A1* | 1/2013 | Koike | A61M 25/09 |
| | | | 604/528 |
| 2014/0052109 A1* | 2/2014 | Organ | A61M 25/0147 |
| | | | 604/528 |
| 2014/0276138 A1* | 9/2014 | Millett | A61B 5/6886 |
| | | | 600/486 |
| 2014/0323918 A1* | 10/2014 | Miyata | A61M 25/09 |
| | | | 600/585 |
| 2014/0358169 A1 | 12/2014 | Terashi et al. | |
| 2015/0088036 A1* | 3/2015 | Takada | A61M 25/09 |
| | | | 600/585 |
| 2017/0239453 A1* | 8/2017 | Kawakita | A61M 25/09 |
| 2018/0064913 A1* | 3/2018 | Ushida | A61M 25/09 |
| 2018/0093070 A1* | 4/2018 | Cottone | A61M 25/09 |
| 2018/0339138 A1* | 11/2018 | Privitera | A61M 25/09 |

FOREIGN PATENT DOCUMENTS

| | | | | |
|---|---|---|---|---|
| CN | 104127950 A | | 11/2014 | |
| JP | 57-45948 U | | 3/1982 | |
| JP | 60-7862 A | | 1/1985 | |
| JP | 60-12069 A | | 1/1985 | |
| JP | 09-510125 A | | 10/1997 | |
| JP | 3971447 B1 | * | 9/2007 | |
| JP | 2011-10900 A | | 1/2011 | |
| JP | 2011206413 A | * | 10/2011 | A61M 25/09 |
| JP | 2014023943 A | * | 2/2014 | A61M 25/09 |
| JP | 2014213126 A | * | 11/2014 | A61M 25/09 |
| JP | 2014-233411 A | | 12/2014 | |
| JP | 2015047451 A | * | 3/2015 | A61M 25/09 |
| JP | 2015047500 A | * | 3/2015 | A61M 25/09 |
| JP | 2015062442 A | * | 4/2015 | |
| JP | 5913383 B2 | * | 4/2016 | A61M 25/09 |
| JP | 2017-169751 A | | 9/2017 | |
| JP | 6344732 B1 | * | 6/2018 | A61M 25/09 |
| KR | 20070036401 A | * | 4/2007 | |
| WO | 1995/24237 A2 | | 9/1995 | |
| WO | WO-03000116 A2 | * | 1/2003 | A61M 25/09 |
| WO | WO-2006126474 A1 | * | 11/2006 | A61B 17/12022 |
| WO | 2009/119386 A1 | | 10/2009 | |
| WO | WO-2010026495 A2 | * | 3/2010 | A61M 25/09 |

* cited by examiner

FIG.3

|  | IN VICINITY OF FIRST INTERMEDIATE FIXING PORTION 61 | | IN VICINITY OF SECOND INTERMEDIATE FIXING PORTION 62 | |
| --- | --- | --- | --- | --- |
|  | FIRST RESIN COATING 71 | SPARSELY WOUND PORTION 22 | FIRST RESIN COATING 71 | SPARSELY WOUND PORTION 22 |
| SAMPLE1 | YES | NO | NO | NO |
| SAMPLE2 | YES | NO | NO | YES |
| SAMPLE3 | NO | NO | NO | NO |
| SAMPLE4 | NO | YES | NO | YES |
| SAMPLE5 | YES | NO | YES | NO |

GUIDEWIRE HAVING EXTERNAL COIL WITH SECTIONS OF DIFFERENT WINDING PITCHES AND RESIN COATINGS

CROSS REFERENCES TO RELATED APPLICATIONS

This application is a bypass continuation of International Application No. PCT/JP2017/035759, filed Sep. 30, 2017, the entire contents of which are incorporated herein by reference.

TECHNICAL FIELD

The present disclosure relates to a guide wire.

BACKGROUND

Conventionally, known is a guide wire used for inserting a catheter into a blood vessel or a digestive organ. A guide wire generally includes: a core shaft including a wire material; and a coil body wound around on an outer periphery of the core shaft, in which the distal end of the core shaft is joined to the distal end of the coil body. For example, in a treatment for expanding a diameter of a vascular lesion site, a guide wire is inserted into a blood vessel, and allowed to advance through the blood vessel until the distal end of the guide wire reaches the vascular lesion site. During this, a rotational followability is required for the guide wire which allows the guide wire to advance in a desired direction through a winding and complex vascular pathway or a breached vascular portion. The term "rotational followability" means that a capability of the distal end portion of a guide wire located inside a blood vessel to rotate in response to the rotational movement of a hand-side portion (the proximal end portion) of the guide wire located outside the body when the hand-side portion is rotated.

For example, Patent Documents 1 to 3 each disclose a guide wire in which the distal end of a coil body is fixed to the distal end of a core shaft, and the proximal end of the coil body is fixed to the proximal end of the core shaft.

CITATION LIST

Patent Document

Patent Document 1: Japanese Patent Application Laid-Open No. S60-7862
Patent Document 2: Japanese Patent Application Laid-Open No. S60-12069
Patent Document 3: Japanese Patent Application Laid-Open No. S57-45948

SUMMARY

The present application provides a guide wire, comprising: a core shaft; a coil wound around the core shaft; a distal-end joining region to which a distal end of the core shaft and a distal end of the coil are joined; and a proximal-end joining region to which a proximal end of the core shaft and a proximal end of the coil are joined, wherein the coil has a sparsely wound portion having a sparser coil pitch than other portions of the coil, the sparsely wound portion being disposed between the distal-end joining region and the proximal-end joining region.

BRIEF DESCRIPTION OF THE DRAWINGS

FIG. 3 shows a table comparing the configurations of the samples 1 to 5 used for the rotational followability tests.

DETAILED DESCRIPTION

Figure 1:
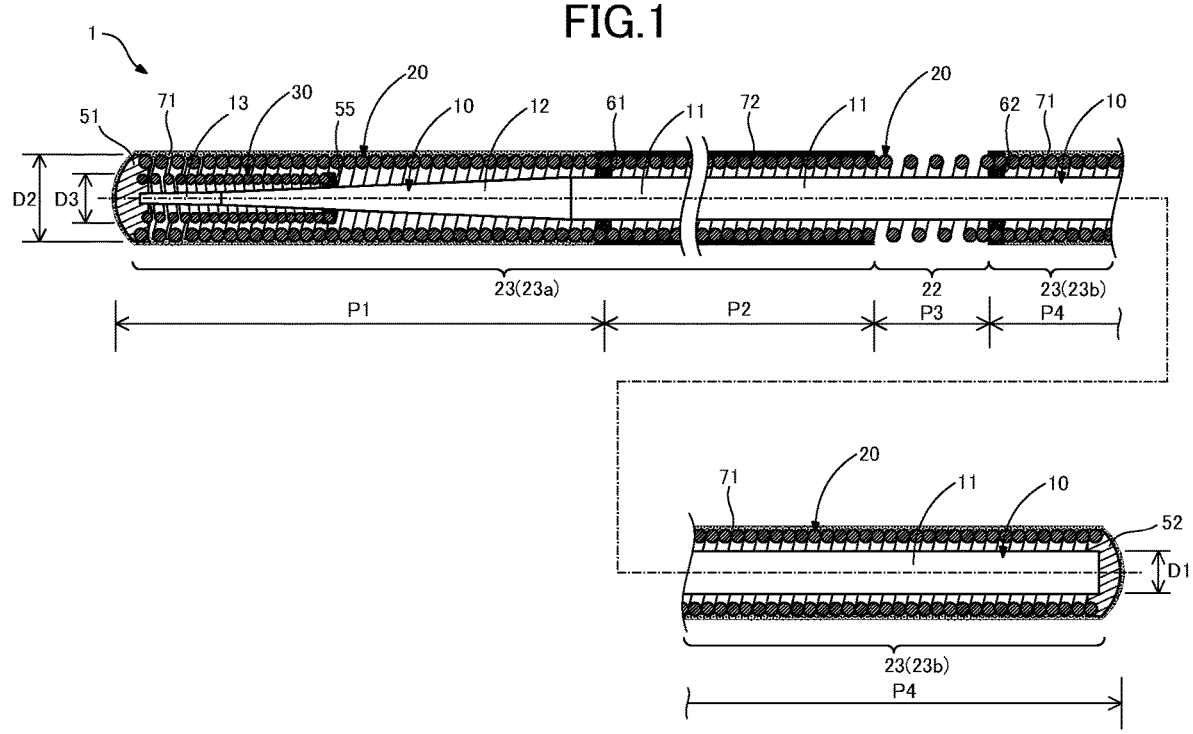
FIG. 1 shows a schematic partial cross-sectional view of the overall configuration of a guide wire according to a first embodiment.

Problems to be Solved by the Disclosure

The guide wires disclosed in Patent Documents 1 to 3, however, fail to provide sufficient rotational followability. Specifically, when a guide wire according to any one of Patent Documents 1 to 3 is curved in the inside of the body, a portion of a coil body located at the inner side of the curvature, i.e., a portion of the coil body located at the side of a direction curved relative to the axis direction of the coil body, may be compressed in the axis direction. This may cause a coil to be squeezed at the compressed portion, resulting in a decreased rotational followability. Further, the inner peripheral portion of the portion of the coil body located at the inner side of the curvature may be brought into contact with the outer peripheral portion of the core shaft. This may result in a state where the core shaft is pulled in the axis direction, which may further decrease rotational followability. It is noted that the aforementioned problems may be significant for a guide wire in which a coil body is wound around a core shaft entirely from the distal end through the proximal end, but may also occur in a guide wire in which a coil body is wound around a core shaft partially but not entirely.

The present disclosure is made in order to solve the above problems. An object of the present disclosure is to provide a technology for preventing a decrease in rotational followability of a guide wire having a coil body wound around a core shaft when the guide wire is curved.

Means for Solving the Problems

The present disclosure is made in order to solve at least partially the aforementioned problems, and can be implemented according to the following aspects.

(1) According to an aspect of the present disclosure, provided is a guide wire. The above guide wire includes: a core shaft; a coil body wound around the core shaft; a distal-end joining region to which a distal end of the core shaft and a distal end of the coil body are joined; and a proximal-end joining region to which a proximal end of the core shaft and a proximal end of the coil body are joined, in which the coil body has a sparsely wound portion having a relatively sparse coil pitch, the sparsely wound portion being disposed between the distal-end joining region and the proximal-end joining region.

According to the above configuration, coil squeezing can be relieved by virtue of a space between turns of a coil at the sparsely wound portion when the guide wire is curved, and a portion of the coil body located at an inner side of the curvature is compressed in the axis direction of the guide wire. This can prevent a decrease in rotational followability when the guide wire is curved. Further, according to the above configuration, coil squeezing due to a curved guide wire can be relieved. This, in turn, can relieve a state where the core shaft is pulled in the axis direction due to contact of the coil body with the core shaft. This also can prevent a decrease in rotational followability when the guide wire is curved.

(2) In the guide wire according to the aspect (1), the coil body may have a closely wound portion having a relatively closer coil pitch than the sparsely wound portion at a distal end side relative to a distal end of the sparsely wound portion and a closely wound portion having a relatively closer coil pitch than the sparsely wound portion at a proximal end side relative to a proximal end of the sparsely wound portion. The above configuration can prevent a decrease in rotational followability when the guide wire is curved by virtue of the sparsely wound portion while preventing a decreased slidability of the guide wire by virtue of the closely wound portion disposed at the both sides.

(3) In the guide wire according to the aspect (1) or (2), the coil body may have a resin coating formed both on an outer surface of the closely wound portion at the distal end side relative to the distal end of the sparsely wound portion and on an outer surface of the closely wound portion at the proximal end side relative to the proximal end of the sparsely wound portion, and the resin coating may be interrupted at the sparsely wound portion. According to the above structure, constraint of the coil body due to the resin coating can be relieved at the sparsely wound portion. This can further prevent a decrease in rotational followability when the guide wire is curved.

(4) In the guide wire according to any one of the above aspects, the closely wound portion at the distal end side relative to the distal end of the sparsely wound portion corresponds to a first closely wound portion, and the closely wound portion at the proximal end side relative to the proximal end of the sparsely wound portion corresponds to a second closely wound portion, and the coil body may have a resin coating formed both on an outer surface of a portion of the first closely wound portion in a predetermined range from the distal end of the first closely wound portion and an outer surface of the second closely wound portion, and the resin coating may be interrupted at the sparsely wound portion and a part of a rear end side of the first closely wound portion. When a resin coating is formed at the first closely wound portion, a resin coating-forming liquid may enter into the core shaft through the sparsely wound portion, causing the coil body to adhere to the core shaft. This can be reduced according to the above configuration where the resin coating is not formed at a part of the rear end side of the first closely wound portion. According to the above configuration, constraint of the coil body due to the resin coating can be relieved at the sparsely wound portion and a part of the rear end side of the first closely wound portion. This can further prevent a decrease in rotational followability when the guide wire is curved.

(5) In the guide wire according to any one of the above aspects, the core shaft may have a largest-outer diameter portion having an outer diameter largest in the core shaft and constant from a proximal end portion toward a distal end portion of the core shaft, and the sparsely wound portion may be disposed in the coil body at a position to cover the largest-outer diameter portion. The above configuration can relieve a state where the core shaft is pulled in the axis direction due to contact of the largest-outer diameter portion with the coil body when the guide wire is curved, and thus can prevent a decrease in rotational followability when the guide wire is curved.

(6) The guide wire according to any one of the above aspects may further include an inner coil body disposed in an inner side of the coil body and wound around the core shaft, in which the inner coil body may be shorter in length than the coil body, and a distal end of the inner coil body may be joined to the distal end of the core shaft at the distal-end joining region, and the sparsely wound portion may be disposed in the coil body at a position to cover a portion of the core shaft around which the inner coil body is not wound. The above configuration can prevent a decrease in rotational followability when the guide wire is curved while preventing occurrence of engagement between an element wire of the inner coil body and an element wire of the coil body.

It is noted that the present disclosure can be implemented according to various aspects. For example, the present disclosure can be implemented in forms of a coil body for use in a guide wire, a method of manufacturing a guide wire, and the like.

First Embodiment

FIG. 1 shows a schematic partial cross-sectional view of the overall configuration of a guide wire 1 according to a first embodiment. The guide wire 1, which is a medical instrument used for inserting a catheter into a blood vessel or a digestive organ, has a core shaft 10, a coil body 20, an inner coil body 30, a distal-end joining region 51, a proximal-end joining region 52, an inner joining region 55, a first intermediate fixing portion 61, a second intermediate fixing portion 62, a first resin coating 71, and a second resin coating 72. Below, the left-hand side of FIG. 1 is defined as the "distal end side" of each of the guide wire 1 and constituent members thereof while the right-hand side of FIG. 1 is defined as the "proximal end side" of each of the guide wire 1 and the constituent members thereof.

The core shaft 10 is a tapered and elongated member having a larger diameter at the proximal end side and a smaller diameter at the distal end side. The core shaft 10 may be formed with, for example, a superelastic alloy such as a stainless steel alloy (SUS302, SUS304, SUS316, and the like) and a Ni—Ti alloy; or a material such as a piano wire, a nickel-chromium based alloy, a cobalt alloy, and tungsten. The core shaft 10 may be formed with a known material other than the above. There is no particular limitation for the length of the core shaft 10, but the length may be, for example, in a range of 600 mm to 3000 mm. The core shaft 10 has a large-diameter portion 11, a tapered portion 12, and a small-diameter portion 13 in this order from the proximal end side toward the distal end side.

The large-diameter portion 11 corresponds to a largest-outer diameter portion having an outer diameter largest in the core shaft 10 and constant from a proximal end of the core shaft 10 toward the distal end side. The proximal-end joining region 52 is formed at a proximal end of the large-diameter portion 11. There is no particular limitation for an outer diameter D1 of the large-diameter portion 11, but D1 may be, for example, in a range of 0.1 mm to 0.5 mm. There is also no particular limitation for the length of the large-diameter portion 11, but the length may be, for example, in a range of 560 mm to 2960 mm.

The tapered portion 12 is formed between the large-diameter portion 11 and the small-diameter portion 13, and has an outer diameter decreasing from a proximal end toward a distal end. The small-diameter portion 13 is formed at a distal end of the core shaft 10, and the distal-end joining region 51 is formed at a distal end of the small-diameter portion 13.

The coil body 20 is composed of a single coil or a member in which a plurality of coils are bundled, and is wound around the core shaft 10 so as to cover almost entirely an outer periphery of the core shaft 10. The coil body 20 is fixed to the core shaft 10 through the distal-end joining region 51, the proximal-end joining region 52, the first intermediate-fixing portion 61, and the second intermediate-fixing portion 62.

A coil of the coil body 20 may be a single coil in which one element wire is spirally wound into a cylindrical shape or may be a hollow twisted-wire coil in which a plurality of element wires are twisted into a cylindrical shape. Alternatively, the coil body 20 may be in combination of a single coil and a hollow twisted-wire coil. The coil body 20 as described in this embodiment is configured to be a single coil at the distal end side relative to the second intermediate fixing portion 62 and a hollow twisted-wire coil at the proximal end side relative to the second intermediate fixing portion 62.

The coil body 20 may be formed with, for example, a superelastic alloy such as a stainless steel alloy (SUS302, SUS304, SUS316, and the like) and a Ni—Ti alloy; a radiolucent alloy such as a piano wire, a nickel-chromium based alloy, a cobalt alloy, and tungsten; a radiopaque alloy such as alloys including these elements (for example, a platinum-nickel alloy). The core body 20 may be formed with a known material other than the above. The length of the coil body 20 is substantially same as that of the core shaft 10. The coil body 20 has an outer diameter D2 which is configured to be constant. There is no particular limitation for the outer diameter D2, but D2 is may be, for example, in a range of 0.3 mm to 1.5 mm.

The distal end of the coil body 20 is joined to the distal end of the core shaft 10 through the distal-end joining region 51. The distal-end joining region 51 may be formed with a metal solder such as a silver solder, a gold solder, zinc, a Sn—Ag alloy, and an Au—Sn alloy. The distal end of the coil body 20 is fixed with and adheres to the distal end of the core shaft 10 through that metal solder. It is noted that the distal-end joining region 51 may be formed with an adhesive such as an epoxy adhesive, and the distal end of the coil body 20 may be fixed with and adheres to the distal end of the core shaft 10 through that adhesive. The proximal end of the coil body 20 is joined to the proximal end of the core shaft 10 through the proximal end joining region 52. The proximal-end joining region 52 may be formed with the same material as the distal-end joining region 51, or may be formed with a different material than the distal-end joining region 51.

A portion in the vicinity of an intermediate portion of the coil body 20 is fixed to the large-diameter portion 11 of the core shaft 10 through the first intermediate fixing portion 61. Another portion in the vicinity of the intermediate portion of the coil body 20 is fixed to the large-diameter portion 11 of the core shaft 10 through the second intermediate fixing portion 62. The second intermediate fixing portion 62 is located at the proximal end side relative to the first intermediate fixing portion 61, and, in this embodiment, corresponds to a connection portion (a boundary portion) between the single coil and the hollow twisted-wire coil of the coil body 20. The first intermediate fixing portion 61 and the second intermediate fixing portion 62 may be formed with the same material as the distal-end joining region 51 and the proximal-end joining region 52, or may be formed with different materials.

The coil body 20 has a sparsely wound portion 22 and closely wound portions (a first closely wound portion 23a, a second closely wound portion 23b), which have different coil pitches. The first closely wound portion 23a, the sparsely wound portion 22, and the second closely wound portion 23b are formed in the coil body 20 in this order from the distal end side toward the proximal end side. In this embodiment, the first closely wound portion 23a and the sparsely wound portion 22 are configured to be the same single coil, and the second closely wound portion 23b is configured to be a hollow twisted-wire coil.

The sparsely wound portion 22 is a portion having a relatively sparse coil pitch in the coil body 20. Specifically, the sparsely wound portion 22 has a sparser coil pitch than the closely wound portions 23 (the first closely wound portion 23a, the second closely wound portion 23b), and, in this embodiment, has a coil pitch which is about 0.80 to 0.99 times of a coil pitch of the first closely wound portion 23a, The term "coil pitch" of the sparsely wound portion 22 as used herein means the average value of coil pitches in the sparsely wound portion 22, and corresponds to a value obtained by dividing the length of the sparsely wound portion 22 in the axis direction by the number of coil turns in the sparsely wound portion 22. The term "coil pitch" of the first closely wound portion 23a as used herein means the average value of coil pitches in the first closely wound portion 23a, and corresponds to a value obtained by dividing the length of the first closely wound portion 23a in the axis direction by the number of coil turns in the first closely wound portion 23a. The sparsely wound portion 22 is disposed at a position where the proximal end thereof is positioned adjacent to the second intermediate fixing portion 62.

The closely wound portions 23 (the first closely wound portion 23a, the second closely wound portion 23b) are each a portion having a relatively close coil pitch in the coil body 20. The first closely wound portion 23a and the second closely wound portion 23b may have the same coil pitch, or may have different coil pitches. The first closely wound portion 23a has a distal end and a proximal end, the distal end being fixed to the distal-end joining region 51, the proximal end being in contact with the distal end of the sparsely wound portion 22. The second closely wound portion 23b has a distal end and a proximal end, the distal end being in contact with the proximal end of the sparsely wound portion 22 and the second intermediate fixing portion 62, the proximal end being fixed to the proximal-end joining region 52.

As described above, the closely wound portions (the first closely wound portion 23a, the second closely wound portion 23b) are arranged in the coil body 20 at the distal end side relative to the distal end of the sparsely wound portion 22 and at the proximal end side relative to the sparsely wound portion 22, respectively. Further, the sparsely wound portion 22 is disposed in the coil body 20 at a position to cover the large-diameter portion 11. Moreover, the sparsely wound portion 22 is disposed in the coil body 20 at a position to cover a portion of the core shaft 10 around which the inner coil body 30 is not wound. An example of the advantageous effects from these will be described below.

The inner coil body 30 includes a single coil or a hollow twisted-wire coil, and is wound around the core shaft 10 so as to cover an outer periphery of the distal end side of the core shaft 10. Here, the inner coil body 30 is wound around the small-diameter portion 13 and a portion of the tapered portion 12 of the core shaft 10. The inner coil body 30 is shorter in length than the core shaft 10 and the coil body 20, and is fixed to the core shaft 10 through the distal-end joining region 51 and the inner joining region 55.

There is no particular limitation for the length of the inner coil body 30, but the length may be, for example, 10 mm to 100 mm. The coil body 30 has an outer diameter D3 which is configured to be constant. There is no particular limitation for the outer diameter D3, but D3 may be, for example, in a range of 0.1 mm to 0.5 mm. The inner coil body 30 has a distal end joined to the distal end of the core shaft 10 through the distal-end joining region 51. The inner coil body 30 has a proximal end joined to the tapered portion 12 of the core shaft 10 through the inner joining region 55. The inner joining region 55 may be formed with the same material as or a different material than the distal-end joining region 51.

The winding direction of the inner coil body 30 may be the same as or different from that of the coil body 20. Further, the coil pitch of the inner coil body 30 may be the same as or different from that of the coil body 20. It is noted that a coil pitch of the inner coil body 30 different from that of the coil body 20 can prevent an engagement events between element wires of these when the distal end portion of the guide wire 1 is curved and deformed.

In the guide wire 1 according to the present embodiment, a portion from the distal end of the guide wire 1 to the first intermediate fixing portion 61 is called a "first segment P1", a portion from the first intermediate fixing portion 61 to the distal end of the sparsely wound portion 22 is called a "second segment P2", a portion from the distal end to the proximal end of the sparsely wound portion 22 is called a "third segment P3", and a portion from the proximal end of the sparsely wound portion 22 to the proximal end of the guide wire 1 is called a "fourth segment P4." The length of the first segment P1 may be, for example, in a range of 40 mm to 400 mm. The length of the second segment P2 may be, for example, in a range of 250 mm to 1000 mm. The length of the third segment P3 may be, for example, in a range of 10 mm to 100 mm. The length of the fourth segment P4 may be, for example, in a range of 300 mm to 1500 mm.

In this case, the coil body 20 has the first closely wound portion 23a formed at the first segment P1 and the second segment P2, the sparsely wound portion 22 formed in the third segment P3, and the second closely wound portion 23b formed at the fourth segment P4. In the coil bodies 20, the outer surfaces of portions located at the first segment P1 and the fourth segment P4 are covered with the first resin coating 71, and the outer surface of a portion located at the second segment P2 is covered with the second resin coating 72. The outer surface of a portion located at the third segment P3 of the coil body 20 does not have a resin coating formed thereon, and thus is exposed.

That is, the guide wire 1 is covered with a resin coating (the first resin coating 71 or the second resin coating 72) at portions other than the sparsely wound portion 22, but not covered with a resin coating at the sparsely wound portion 22. In other words, the coil body 20 has a resin coating formed on the outer surfaces of the first closely wound portion 23a and the second closely wound portion 23b, and the resin coating is interrupted at the sparsely wound portion 22. An example of the advantageous effects from this will be described below.

The first resin coating 71 may include a hydrophobic resin which is less frictional against the outside than the surface of the coil body 20, and includes a silicon resin or the like in this embodiment. It is noted that polyurethane, polyethylene, polyvinyl chloride, polyester, polypropylene, polyamide, polystyrene, and the like may be used as a hydrophobic resin in addition to a silicon resin.

The second resin coating 72 may include a resin having a hydrophilic group, for example, a resin based on starch such as a carboxylmethyl starch; cellulose such as carboxyl methyl cellulose; polysaccharide such as alginic acid, heparin, chitin, chitosan, and hyaluronic acid; a natural water-soluble polymeric material such as gelatin; or a synthetic water-soluble polymeric material such as polyvinyl alcohol, polyethylene oxide, polyethylene glycol, polypropylene glycol, polyacrylate, methyl vinyl ether-maleic anhydride copolymer, methyl vinyl ether-maleic anhydride salt, methyl vinyl ether-maleic anhydride ammonium salt, maleic anhydride-ethyl ester copolymer, poly hydroxyethyl phthalic acid ester copolymer, poly(dimethylol propionate), polyacrylamide, a polyacrylamide quaternary compound, polyvinylpyrrolidone, polyethyleneimine, polyethylene sulfonate, and water-soluble nylon. The second resin coating 72 swells upon absorbing water, leading to superior sliding properties and anti-thrombus adhesion than the first resin coating 71.

The second resin coating 72 has better lubricity than the first resin coating 71, and can further reduce frictional resistance in the body. On the other hand, when the outer surface from the distal end through the proximal end of the guide wire is entirely covered with the second resin coating 72, the resulting guide wire may be excessively slippery in the body, resulting in decreased operativity at a branch portion in the living body and the like. The configuration according to the present embodiment can improve operativity where the first resin coating 71 is disposed at the distal end side and proximal end side of the guide wire, and the second resin coating 72 is disposed at a portion of the intermediate portion.

Examples of Advantageous Effects of Present Embodiment

In the guide wire 1 according to the present embodiment as described above, the coil body 20 has the sparsely wound portion 22 between the distal-end joining region 51 and the proximal-end joining region 52. This can prevent a decrease in rotational followability of the guide wire due to curvature. The term "rotational followability" means a capability of the distal end of a guide wire to rotate in response to rotation of the proximal end of the guide wire. In other words, the rotational followability is a capability of transmitting rotation through a core shaft and a coil body.

In the guide wire 1 according to the present embodiment, coil squeezing can be relieved by virtue of a space between turns of a coil at the sparsely wound portion 22 when the guide wire 1 is curved, and a portion of the coil body 20 located at the inner side of the curvature is compressed in the axis direction of the guide wire 1. This can prevent a decrease in rotational followability when the guide wire 1 is curved, and coil squeezing occurs. Moreover, coil squeezing can be relieved by virtue of the sparsely wound portion 22 when the guide wire 1 is curved. This, in turn, can relieve pulling of the core shaft 10 in the axis direction due to contact of the coil body 20 with the core shaft 10. This can also prevent a decrease in rotational followability due to pulling of the core shaft 10 in the axis direction when the inner periphery of the coil body 20 is brought into contact with the outer periphery of the core shaft 10. The guide wire 1 according to the present embodiment can prevent a decrease in rotational followability due to curvature. This will be further described below with reference to FIGS. 2 to 5.

Further, the configuration of the guide wire 1 according to the present embodiment where the coil body 20 has the closely wound portions 23, one at the distal end side relative to the distal end of the sparsely wound portion 22 and the other at the proximal end side relative to the proximal end of the sparsely wound portion 22, can prevent a decrease in rotational followability of the guide wire 1 due to curvature by virtue of the sparsely wound portion 22 while preventing a decrease in slidability of the guide wire 1 by virtue of the closely wound portions 23 disposed at the both sides. The coil body generally has a higher slidability at the closely wound portions than the sparsely wound portion. The guide wire 1 according to the present embodiment can prevent a decrease in rotational followability of the guide wire 1 due to curvature by virtue of the sparsely wound portion 22 while maintaining slidability by virtue of the closely, wound portions 23 disposed at the both sides of the sparsely wound portion 22.

Moreover, the configuration of the guide wire 1 according to the present embodiment, where the coil body 20 has the resin coatings 71, 72 formed on the respective outer surface of the first closely wound portion 23a at the distal end side relative to the distal end of the sparsely wound portion 22 and the outer surface of the second closely wound portion 23b at the proximal end side relative to the proximal end of the sparsely wound portion 22, respectively, and the resin coatings 71, 72 are interrupted at the sparsely wound portion 22, can further prevent a decrease in rotational followability when the guide wire 1 is curved. When a resin coating is formed on the outer surface of a coil body, the resin coating generally restricts relative movement of turns of a coil (the coil body is constrained). When the coil body is constrained by the resin coating, the rotational followability of the guide wire may be further decreased when curved. In the guide wire 1 according to the present embodiment, a resin coating is not formed at the sparsely, wound portion 22. Therefore, constraint of the coil body 20 at the sparsely wound portion 22 due to a resin coating can be relieved. This can further prevent a decrease in rotational followability when the guide wire 1 is curved. Further, when a resin coating is formed on the outer surface of the sparsely wound portion 22, the coil body 20 may adhere to the core shaft 10 via a resin coating-forming liquid for forming the resin coating which may enter into the core shaft 10 through the sparsely wound portion 22. This may decrease rotational followability. The lack of a resin coating at the sparsely wound portion 22 can prevent occurrence of adhesion of the coil body 20 with the core shaft 10.

Further, the configuration of the guide wire 1 according to the present embodiment where the sparsely wound portion 22 is disposed in the coil body 20 at a position to cover the large-diameter portion 11 as a largest-outer diameter portion can relieve a state where the core shaft 10 is pulled in the axis direction due to contact between the largest-outer diameter portion and the coil body 20 when the guide wire is curved. This can prevent a decrease in rotational followability when the guide wire is curved.

Moreover, the configuration of the guide wire 1 according to the present embodiment where the sparsely wound portion 22 is disposed in the coil body 20 at a position to cover a portion of the core shaft 10 around which the inner coil body 30 is not wound can prevent a decrease in rotational followability of the guide wire 1 when the guide wire 1 is curved while preventing occurrence of engagement between an element wire of the inner coil body 30 and an element wire of the coil body 20.

Rotational Followability Tests

The guide wire according to the present embodiment can prevent a decrease in rotational followability due to curvature. This will be described with reference to FIGS. 2 to 5. Here, in order to prove the advantageous effects of the guide wire according to the present embodiment, rotational followability tests were performed on five samples including a guide wire having the configuration according to the present embodiment. In the rotational followability tests, the rotational followability of a guide wire is quantitatively measured.

Figure 2:
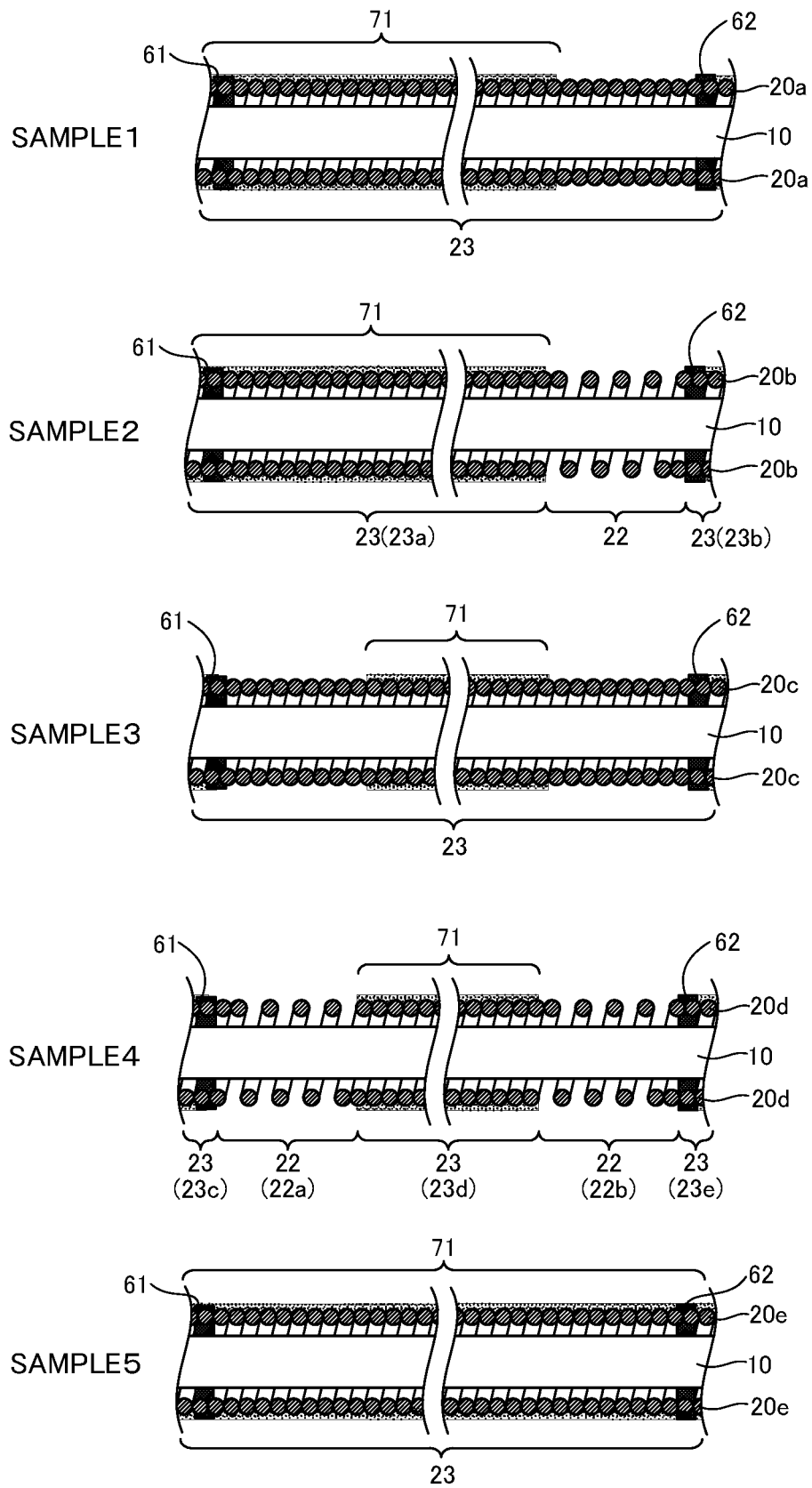
FIG. 2 illustrates the configurations of samples 1 to 5 used for rotational followability tests.

FIG. 2 illustrates the configurations of samples 1 to 5 used for the rotational followability tests. FIG. 2 shows only a portion of each sample between the first intermediate fixing portion 61 and the second intermediate fixing portion 62. FIG. 3 shows a table comparing the configurations of the samples 1 to 5. The samples 1 to 5 each have the core shaft 10, the coil body 20 (20a to 20e), the first intermediate fixing portion 61, the second intermediate fixing portion 62, and the first resin coating 71 as in the guide wire 1 according to the present embodiment as described above (FIG. 1). The samples 1 to 5 differ from each other in the configuration of a portion between the first intermediate fixing portion 61 and the second intermediate fixing portion 62. The remaining portions have the same configurations as the present embodiment (FIG. 1). The samples 1 to 5 differ from each other in the combination of the presence or absence of the first resin coating 71 and the presence or absence of the sparsely wound portion 22 in the vicinity of the first intermediate fixing portion 61 and the second intermediate fixing portion 62.

As shown in FIG. 2, a portion between the first intermediate fixing portion 61 and the second intermediate fixing portion 62 of the coil body 20a of the sample 1 is entirely configured to be as the closely wound portion 23. Further, the coil body 20a does not have the first resin coating 71 formed thereon in the vicinity of the second intermediate fixing portion 62, and thus is exposed. The remaining portion, however, has the first resin coating 71 formed thereon. Accordingly, the sample 1 in the table of FIG. 3 shows "Yes" for the first resin coating 71 and "No" for the sparsely wound portion 22 in the vicinity of the first intermediate fixing portion 61. Further, it shows "No" for the first resin coating 71 and "No" for the sparsely wound portion 22 in the vicinity of the second intermediate fixing portion 62.

As shown in FIG. 2, the coil body 20b of the sample 2 has the sparsely wound portion 22 formed in the vicinity of the second intermediate fixing portion 62, and the remaining portion is configured to be as the closely wound portion 23. Further, the coil body 20b does not have the first resin coating 71 formed thereon in the vicinity of the second intermediate fixing portion 62, and thus is exposed as in the sample 1. The remaining portion, however, has the first resin coating 71 formed thereon. Accordingly, the sample 2 in the table of FIG. 3 shows "Yes" for the first resin coating 71 and "No" for the sparsely wound portion 22 in the vicinity of the first intermediate fixing portion 61. Further, it shows "No" for the first resin coating 71 and "Yes" for the sparsely wound portion 22 in the vicinity of the second intermediate fixing portion 62. The sample 2 is configured as in the guide wire 1 according to the first embodiment except that a resin coating between the first intermediate fixing portion 61 and the second intermediate fixing portion 62 is of the same type as the first resin coating 71.

As shown in FIG. 2, a portion between the first intermediate fixing portion 61 and the second intermediate fixing portion 62 of the coil body 20c of the sample 3 is entirely configured to be as the closely wound portion 23 as in the coil body 20a of the sample 1. In contrast, the coil body 20c does not have the first resin coating 71 formed thereon in the vicinity of the first intermediate fixing portion 61 or in the vicinity of the second intermediate fixing portion 62, and thus is exposed. The remaining portion, however, has the first resin coating 71 formed thereon. Accordingly, the sample 3 in the table of FIG. 3 shows "No" for the first resin coating 71 and "No" for the sparsely wound portion 22 in the vicinity of the first intermediate fixing portion 61. Further, it shows "No" for the first resin coating 71 and "No" for the sparsely wound portion 22 in the vicinity of the second intermediate fixing portion 62.

As shown in FIG. 2, the coil body 20d of the sample 4 has the sparsely wound portions 22 (the first sparsely wound portion 22a, the second sparsely wound portion 22b) formed both in the vicinity of the first intermediate fixing portion 61 vicinity and in the vicinity of the second intermediate fixing portion 62, respectively. In contrast, the coil body 20d does not have the first resin coating 71 formed thereon in the vicinity of the first intermediate fixing portion 61 or in the vicinity of the second intermediate fixing portion 62, and thus is exposed. The remaining portion, however, has the first resin coating 71 formed thereon. Accordingly, the sample 4 in the table of FIG. 3 shows "No" for the first resin coating 71 and "Yes" for the sparsely wound portion 22 in the vicinity of the first intermediate fixing portion 61. Further, it shows "No" for the first resin coating 71 and "Yes" for the sparsely wound portion 22 in the vicinity of the second intermediate fixing portion 62.

As shown in FIG. 2, a portion between the first intermediate fixing portion 61 and the second intermediate fixing portion 62 of the coil body 20e of the sample 5 is entirely configured to be as the closely wound portion 23 as in the coil body 20a of the sample 1. In contrast, the coil body 20e has the first resin coating 71 formed entirely between the first intermediate fixing portion 61 and the second intermediate fixing portion 62. Accordingly, the sample 5 in the table of FIG. 3 shows "Yes" for the first resin coating 71 and "No" for the sparsely wound portion 22 in the vicinity of the first intermediate fixing portion 61. Further, it shows "Yes" for the first resin coating 71 and "No" for the sparsely wound portion 22 in the vicinity of the second intermediate fixing portion 62.

Figure 4:
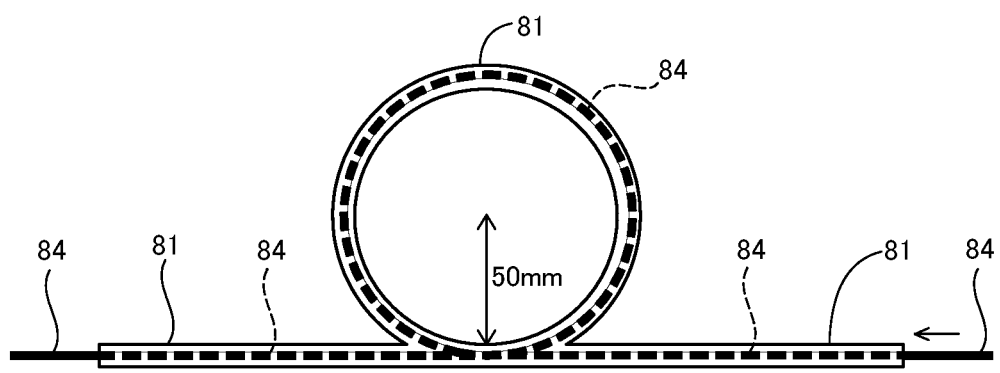
FIG. 4 shows how the rotational followability tests are performed.

FIG. 4 shows how the rotational followability tests are performed. A tube 81 was used to form a circular ring with a radius of 50 mm, and also form a test pathway linearly extending before and after the ring. A guide wire 84 as a sample was inserted through one opening (an opening in the right-hand side in FIG. 4) of the test pathway. The guide wire 84 as a sample was pushed forward until the distal end exits from the other opening of the tube 81. While maintaining this state, the proximal end side of the guide wire 84 was rotated. For each of the samples 1 to 5, the number of rotations at the distal end side was measured when the proximal end side was rotated.

Figure 5:
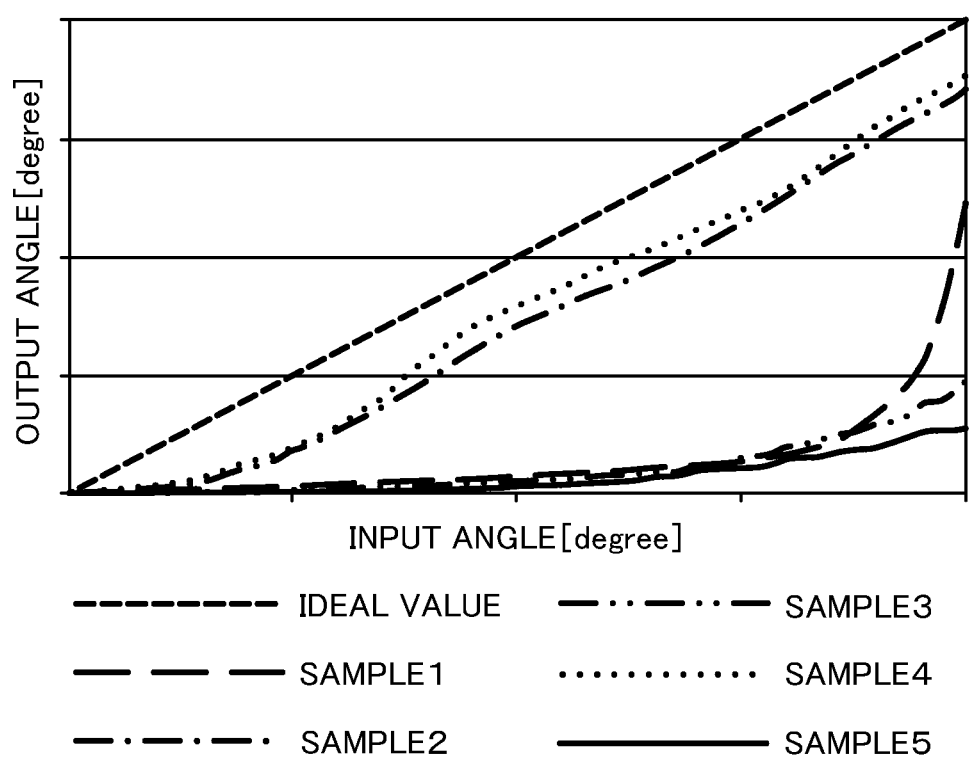
FIG. 5 shows test results from the rotational followability tests.

FIG. 5 shows test results from the rotational followability tests. In a graph of FIG. 5, the horizontal axis represents a rotation angle (an input angle) at the proximal end side of a sample, and the vertical axis represents a rotation angle (an output angle) at the distal end side of the sample. The label "ideal value" in FIG. 5 represents the perfect followability of the distal end side in response to the rotation of the proximal end side. The samples 1, 3, and 5 in which the sparsely wound portion 22 is not formed in the coil body 20 show relatively low rotational followability while the samples 2 and 4 in which the sparsely wound portion 22 is formed in the coil body 20 show relatively high rotational followability. These results reveal that provision of the sparsely wound portion 22 in the coil body 20 can prevent a decrease in rotational followability of a guide wire when the guide wire is curved.

Second Embodiment

Figure 6:
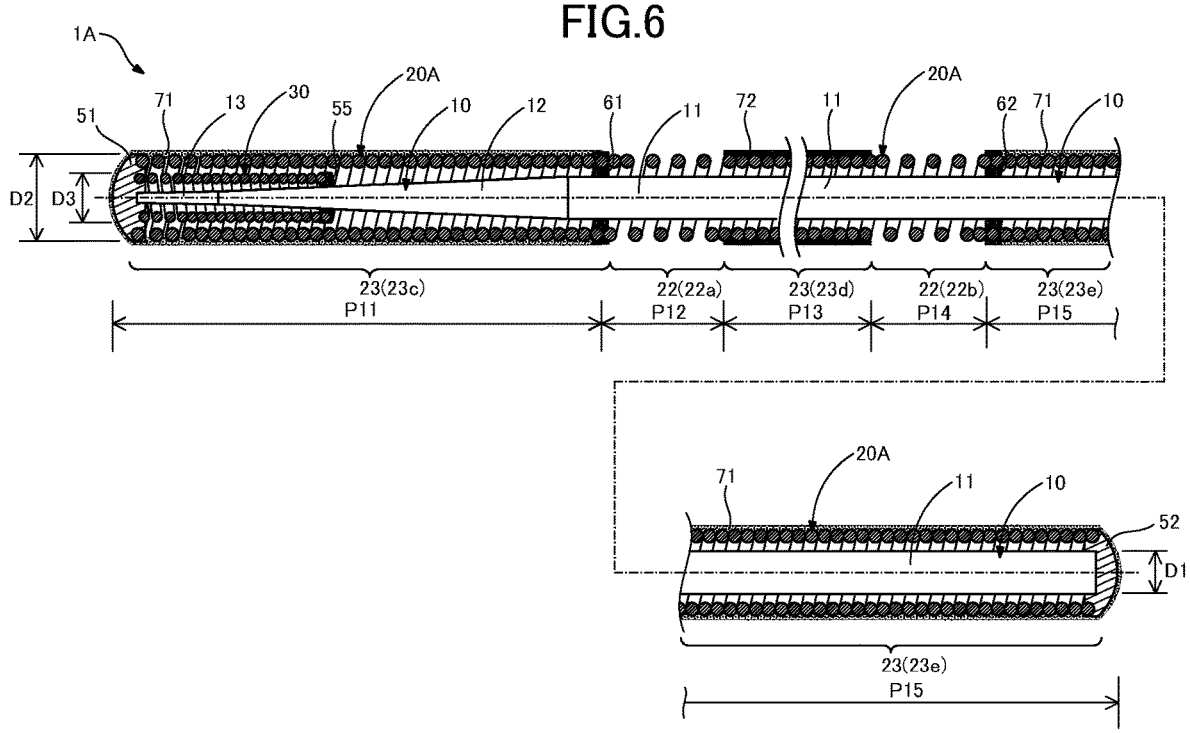
FIG. 6 shows a schematic partial cross-sectional view of the overall configuration of a guide wire according to a second embodiment.

FIG. 6 shows a schematic partial cross-sectional view of the overall configuration of a guide wire 1A according to a second embodiment. The guide wire 1 according to the first embodiment has the sparsely wound portion 22 formed at only one position adjacent to the second intermediate fixing portion 62 (FIG. 1). However, the sparsely wound portion 22 may be formed at a position other than the position adjacent to the second intermediate fixing portion 62, or may be formed at a plurality of positions. For example, the guide wire 1A according to the second embodiment as shown in FIG. 6 has the sparsely wound portions 22 (the first sparsely wound portion 22a, the second sparsely wound portion 22b) formed in the coil body 20A both in the vicinity of the first intermediate fixing portion 61 and in the vicinity of the second intermediate fixing portion 62, respectively. The first sparsely wound portion 22a is disposed at a position where the distal end thereof is positioned adjacent to the first intermediate fixing portion 61. The second sparsely wound portion 22b is disposed at a position where the proximal end thereof is positioned adjacent to the second intermediate fixing portion 62. A first closely wound portion 23c, the first sparsely wound portion 22a, a second closely wound portion 23d, the second sparsely wound portion 22b, and a third closely wound portion 23e are formed in the coil body 20A in this order from the distal end side toward the proximal end side.

In this embodiment, a portion from the distal end of the guide wire 1A to the first intermediate fixing portion 61 is called a "first segment P11", a portion from the first intermediate fixing portion 61 to the proximal end of the first sparsely wound portion 22a is called a "second segment P12", a portion from the proximal end of the first sparsely wound portion 22a to the distal end of the first sparsely wound portion 22b is called a "third segment P13", a portion from the distal end of the second sparsely wound portion 22b to the second intermediate fixing portion 62 is called a "fourth segment P14," and a portion from the second intermediate fixing portion 62 to the proximal end of the guide wire 1A is called a "fifth segment P15."

In this case, the coil body 20A has the first closely wound portion 23c formed at the first segment P11, the first sparsely wound portion 22a formed at the second segment P12, the second closely wound portion 23d formed at the third segment P13, the second sparsely wound portion 22b formed at the fourth segment P14, and the third closely wound portion 23e formed at the fifth segment P15. In the coil body 20A, the outer surfaces of portions located at the first segment P11 and the fifth segment P15 are covered with the first resin coating 71, and the outer surface of a portion located at the third segment P13 is covered with the second resin coating 72. The outer surfaces of portions located at the second segment P12 and the fourth segment P14 of the coil body 20A do not have a resin coating formed thereon, and thus are exposed.

The guide wire 1A according to the second embodiment can also prevent a decrease in rotational followability when the guide wire is curved. Specifically, the guide wire 1A according to the second embodiment is configured as in the sample 4 used in the aforementioned rotational followability tests except for the configuration of the resin coatings. The sample 4 used in the aforementioned rotational followability tests has high rotational followability. Therefore, it is obvious that the guide wire 1A according to the second embodiment can also prevent a decrease in rotational followability of the guide wire when the guide wire is curved. It is noted that the sparsely wound portions 22 may be formed at any portions regardless of the positions of the intermediate fixing portions (the first intermediate fixing portion 61, the second intermediate fixing portion 62). The sparsely wound portion 22 may also be formed at the distal end of the guide wire. However, the sparsely wound portion 22 is preferably disposed in the vicinity of an intermediate portion of a guide wire.

Third Embodiment

Figure 7:
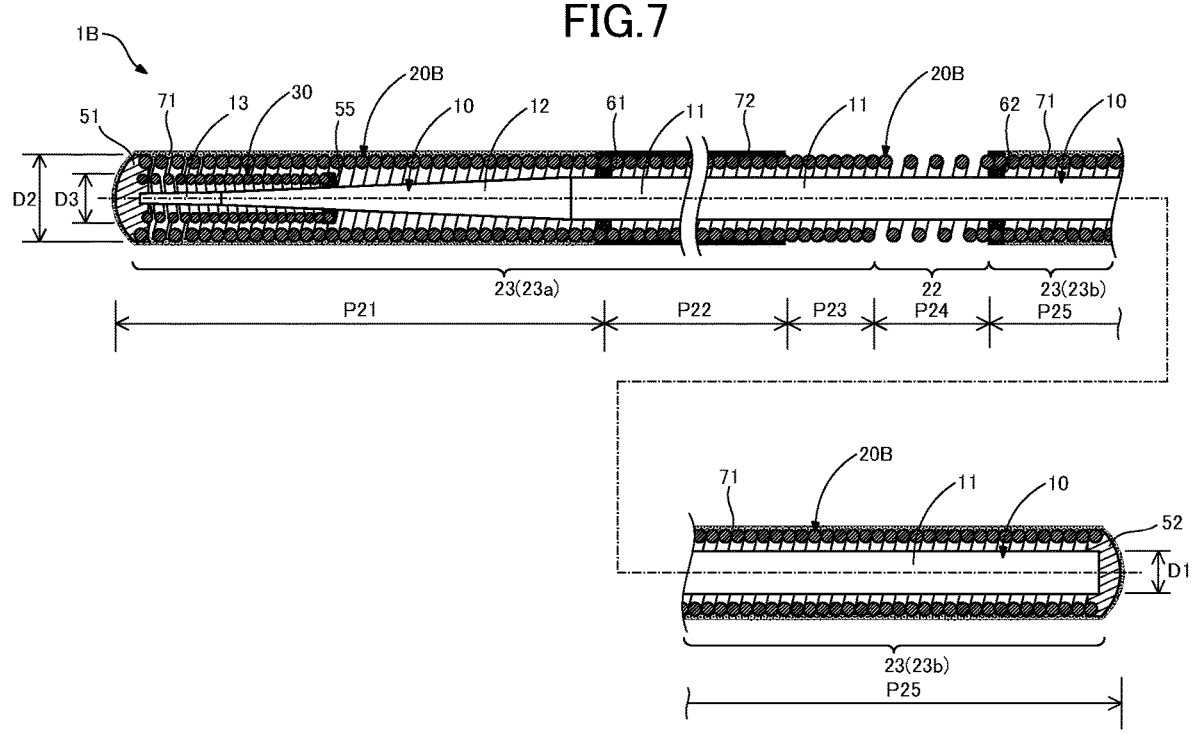
FIG. 7 shows a schematic partial cross-sectional view of the overall configuration of a guide wire according to a third embodiment.

FIG. 7 shows a schematic partial cross-sectional view of the overall configuration of a guide wire 1B according to a third embodiment. The guide wire 1 according to the first embodiment has a resin coating formed entirely on the outer surfaces of the closely wound portions 23 (the first closely wound portion 23a, the second closely wound portion 23b). However, a resin coating does not need to be formed at a portion of the outer surfaces of the closely wound portions 23. For example, in the guide wire 1B according to the third embodiment as shown in FIG. 7, the coil body 20B has a resin coating (the first resin coating 71 or the second resin coating 72) formed on the outer surface of a portion in a predetermined range from the distal end to the proximal end of the first closely wound portion 23a. But the outer surface of a portion of the rear end side of the first closely wound portion 23a does not have a resin coating formed thereon, and thus is exposed. The configurations except for this are similar to those of the guide wire 1 according to the first embodiment. In other words, the coil body 20B has a resin coating formed on the outer surface of a portion in a predetermined range from the distal end of the first closely wound portion 23a and the outer surface of the second closely wound portion 23b, and the resin coating is interrupted at the sparsely wound portion 22 and a portion at the rear end side of the first closely wound portion 23a.

In this embodiment, a portion from the distal end of the guide wire 1B to the first intermediate fixing portion 61 is called a "first segment P21", a portion from the first intermediate fixing portion 61 to a halfway point of the rear end side of the first closely wound portion 23a is called a "second segment P22," a portion from the halfway point of the rear end side of the first closely wound portion 23a to the distal end of the sparsely wound portion 22 is called a "third segment P23," a portion from the distal end to the proximal end of the sparsely wound portion 22 is called a "fourth segment P24", and a portion from the proximal end of the sparsely wound portion 22 to the proximal end of the guide wire 1B is called a "fifth segment P25."

In this case, the coil body 20B has the first closely wound portion 23a formed at the first segment P21, the second segment P22, and the third segment P23; the sparsely wound portion 22 formed at the fourth segment P24; and the second closely wound portion 23b formed at the fifth segment P25. In the coil body 20B, the outer surfaces of portions located at the first segment P21 and the fifth segment P25 are covered with the first resin coating 71, and the outer surface of a portion located at the second segment P22 is covered with the second resin coating 72. The outer surfaces of portions located at the third segment P23 and the fourth segment P24 of the coil body 20B do not have a resin coating formed thereon, and thus are exposed.

The guide wire 1B according to the third embodiment can also prevent a decrease in rotational followability when the guide wire is curved. Further, when a resin coating is formed on the outer surface of the coil body 20, the coil body 20 may adhere to the core shaft 10 via a resin coating-forming liquid for forming the resin coating which may enter into the core shaft 10 through the outer surface of the coil body 20. This may result in a state where rotational followability is decreased. However, the configuration according to the third embodiment can prevent occurrence of such a state. Specifically, when a resin coating-forming liquid is applied on the boundary position between the first closely wound portion 23a and the sparsely wound portion 22 in order to form a resin coating entirely at the closely wound portion 23a, the resin coating-forming liquid may enter unintentionally into the core shaft 10 through the outer surface of the sparsely wound portion 22 by the action of capillary phenomenon and the like. This may cause the coil body 20 to adhere to the core shaft 10, resulting in decreased rotational followability. The configuration of the guide wire 1B according to the third embodiment where a resin coating is formed only at a portion of the first closely wound portion 23 in a predetermined range from the distal end (the second segment P22), but not at a portion of the rear end side (the third segment P23) can prevent a resin coating-forming liquid from unintentionally entering into the core shaft 10 through the outer surface of the sparsely wound portion 22 during manufacture. It is noted that in addition to the above positions, the first closely wound portion 23a may have a portion where a resin coating is not formed. Moreover, no resin coating may be formed at a portion in a predetermined range from the distal end of the second closely wound portion 23b.

Fourth Embodiment

Figure 8:
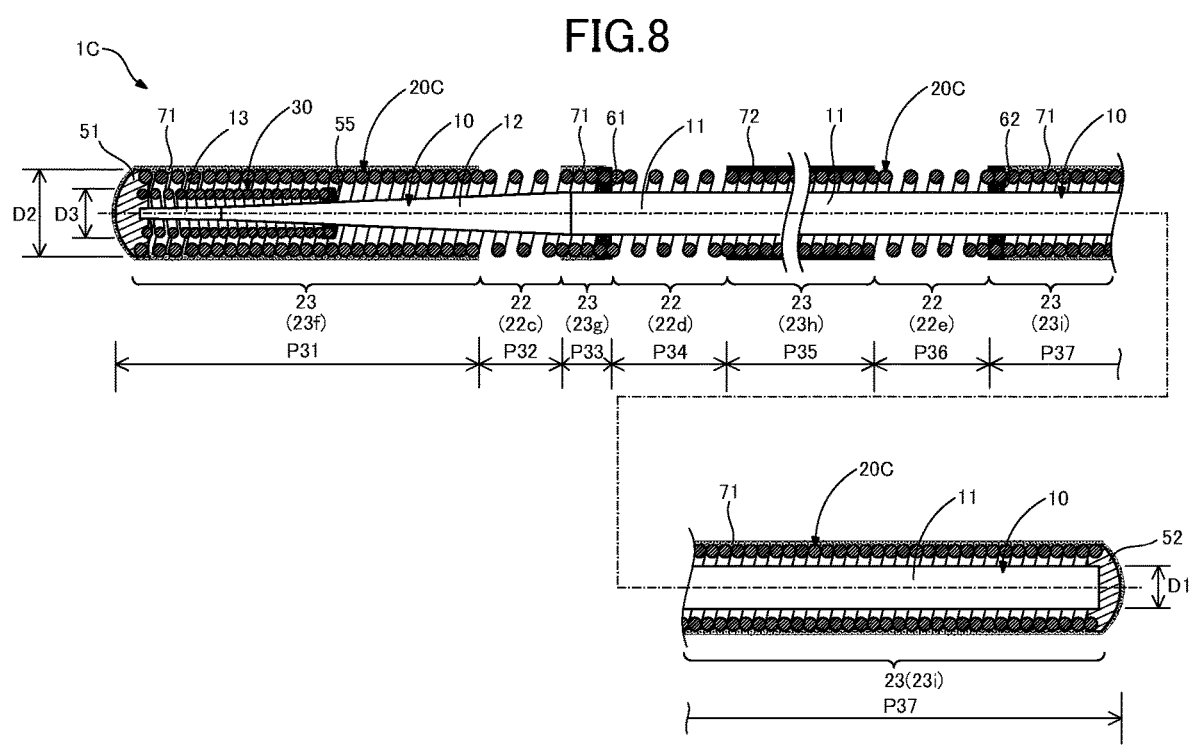
FIG. 8 shows a schematic partial cross-sectional view of the overall configuration of a guide wire according to a fourth embodiment.

FIG. 8 shows a schematic partial cross-sectional view of the overall configuration of a guide wire 1C according to a fourth embodiment. The guide wire 1 according to the first embodiment includes one sparsely wound portion 22 (FIG. 1), and the guide wire 1A according to the second embodiment includes two sparsely wound portions 22 (FIG. 6). However, the number of the sparsely wound portions 22 shall not be limited to these. For example, in the guide wire 1C according to the fourth embodiment as shown in FIG. 8, the coil body 20C has the sparsely wound portions 22 formed in the vicinity of the first intermediate fixing portion 61 and in the vicinity of the second intermediate fixing portion 62 as well as at a portion between the distal end of the guide wire 1C and the first intermediate fixing portion 61. That is, the coil body 20C according to the fourth embodiment has three sparsely wound portions 22 (a first sparsely wound portion 22c, a second sparsely wound portion 22d, a third sparsely wound portion 22e), and a first closely wound portion 23f, the first sparsely wound portion 22c, a second closely wound portion 23g, the second sparsely wound portion 22d, a third closely wound portion 23h, the third sparsely wound portion 22e, and a fourth closely wound portion 23i are formed in this order from the distal end side toward the proximal end side.

In this embodiment, a portion from the distal end of the guide wire 1C to the distal end of the first sparsely wound portion 22c is called a "first segment P31", a portion from the distal end to the rear end of the first sparsely wound portion 22c is called a "second segment P32", a portion from the rear end of the first sparsely wound portion 22c to the first intermediate fixing portion 61 is called a "third segment P33", a portion from the first intermediate fixing portion 61 to the proximal end of the second sparsely wound portion 22d is called a "fourth segment P34", a portion from the proximal end of the second sparsely wound portion 22d to the distal end of the third sparsely wound portion 22e is called a "fifth segment P35", a portion from the distal end of the third sparsely wound portion 22e to the second intermediate fixing portion 62 is called a "sixth segment P36", and a portion from the second intermediate fixing portion 62 to the proximal end of the guide wire 1C is called a "seventh segment P37."

In this case, the coil body 20C has the first closely wound portion 23f formed at the first segment P31, the first sparsely wound portion 22c formed at the second segment P32, the second closely wound portion 23g formed at the third segment P33, the second sparsely wound portion 22d formed at the fourth segment P34, the third closely wound portion 23h formed at the fifth segment P35, the third sparsely wound portion 22e formed at the sixth segment P36, and the fourth closely wound portion 23i formed at the seventh segment P37. In the coil bodies 20C, the outer surfaces of portions located at the first segment P31, the third segment P33, and the seventh segment P37 are covered with the first resin coating 71, and the outer surface of a portion located at the fifth segment P35 is covered with the second resin coating 72. The outer surfaces of portions located at the second segment P32, the fourth segment P34, and the sixth segment P36 of the coil body 20C do not have a resin coating formed thereon, and thus are exposed.

The guide wire 1C according to the fourth embodiment can also relieve coil squeezing due to curvature by virtue of a space between turns of a coil at the three sparsely wound portions 22 (the first sparsely wound portion 22c, the second sparsely wound portion 22d, the third sparsely wound portion 22e). Further, the relieved coil squeezing can, in turn, relieve pulling of the core shaft 10 in the axis direction due to contact of the coil body 20C with the core shaft 10. Therefore, the guide wire 1C according to the fourth embodiment can also prevent a decrease in rotational followability when the guide wire is curved. It is noted that the guide wire may include four or more sparsely wound portions 22.

Fifth Embodiment

Figure 9:
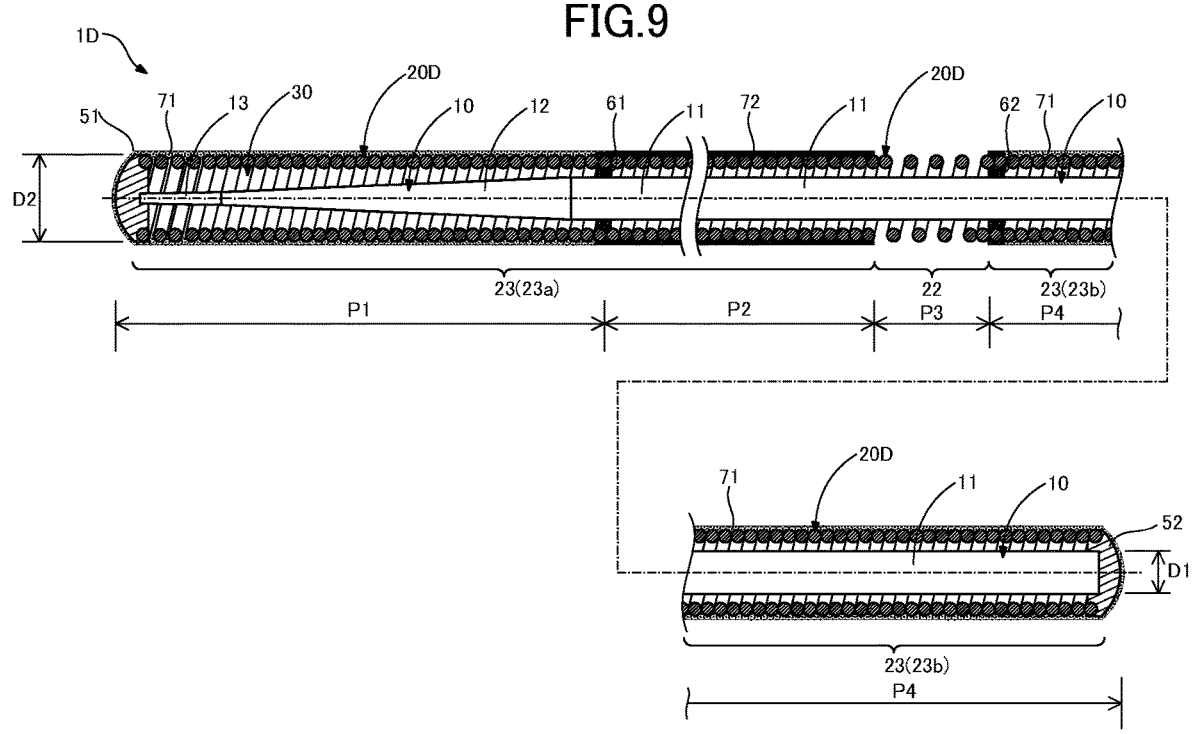
FIG. 9 shows a schematic partial cross-sectional view of the overall configuration of a guide wire according to a fifth embodiment.

FIG. 9 shows a schematic partial cross-sectional view of the overall configuration of a guide wire 1D according to a fifth embodiment. The guide wire 1 according to the first embodiment includes the inner coil body 30 (FIG. 1). However, the inner coil body does not need to be included as in the case of the guide wire 1D according to the fifth embodiment as shown in FIG. 9. Even this configuration can relieve coil squeezing due to curvature by virtue of the sparsely wound portion 22. Further, this can also relieve pulling of the core shaft 10 in the axis direction due to contact of the coil body 20D with the core shaft 10 when curved. Therefore, the guide wire 1D according to the fifth embodiment can also prevent a decrease in rotational followability when the guide wire is curved.

Sixth Embodiment

Figure 10:
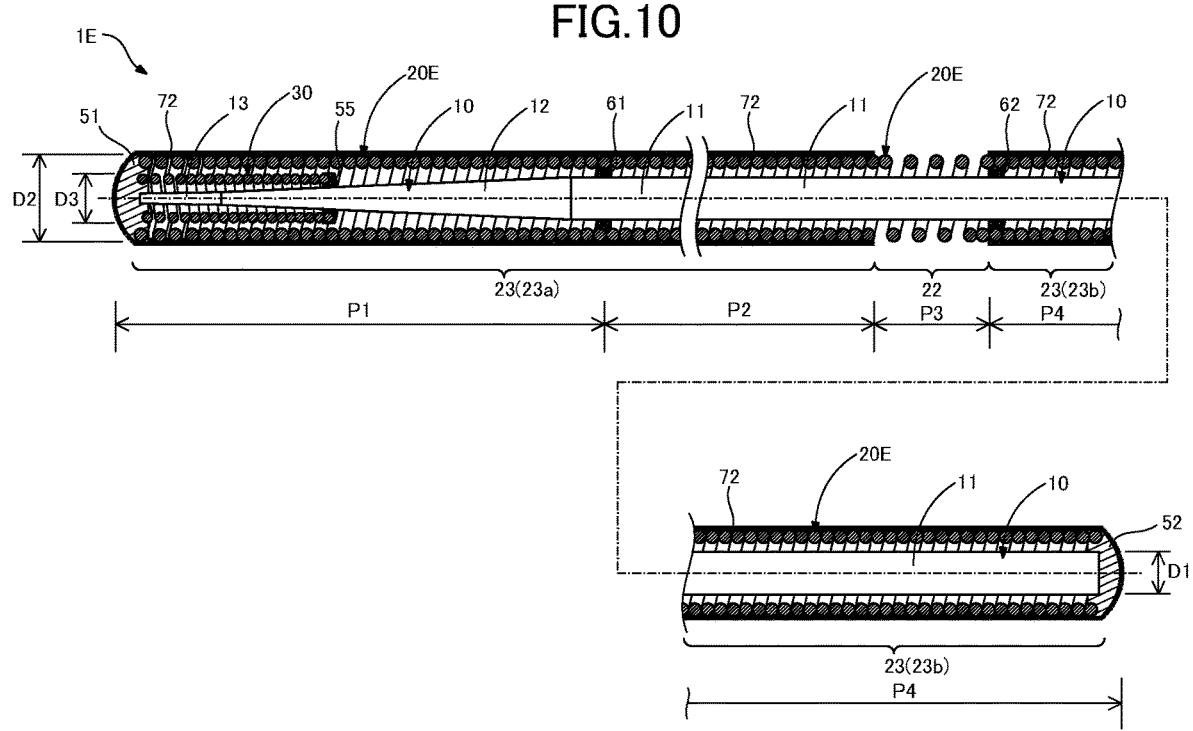
FIG. 10 shows a schematic partial cross-sectional view of the overall configuration of a guide wire according to a sixth embodiment.

FIG. 10 shows a schematic partial cross-sectional view of the overall configuration of a guide wire 1E according to a sixth embodiment. In the guide wire 1 according to the first embodiment, two types of resin coatings (the first resin coating 71, the second resin coating 72) are formed on the outer surface of the coil body 20 (FIG. 1). However, the configuration of a coating formed on the outer surface of the coil body 20 shall not be limited to this. For example, the entire portion except for the sparsely wound portion 22 of the coil body 20E may be covered with a single type of resin coating (the second resin coating 72 in this case) as in the guide wire 1E according to the sixth embodiment as shown in FIG. 10. Further, the guide wire 1 may be covered with three or more types of resin coatings. Even these configurations can prevent a decrease in rotational followability by virtue of the sparsely wound portion 22 when the guide wire is curved.

Seventh Embodiment

Figure 11:
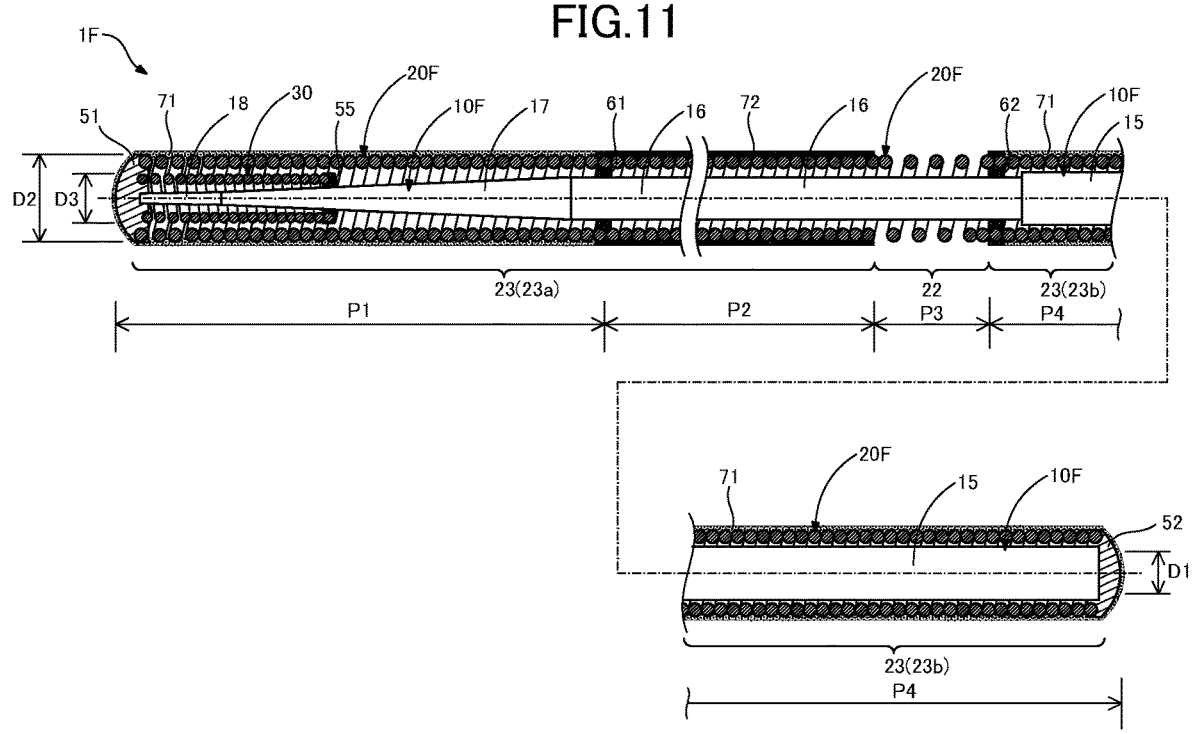
FIG. 11 shows a schematic partial cross-sectional view of the overall configuration of a guide wire according to a seventh embodiment.

FIG. 11 shows a schematic partial cross-sectional view of the overall configuration of a guide wire IF according to a seventh embodiment. In the guide wire 1 according to the first embodiment, the sparsely wound portion 22 of the coil body 20 is disposed at a position to cover the large-diameter portion 11 which corresponds to a largest-outer diameter portion of the core shaft 10 (FIG. 1). However, the sparsely wound portion 22 of the coil body 20 does not need to be disposed at a position to cover the largest-outer diameter portion of the core shaft 10. For example, in the guide wire IF according to the seventh embodiment as shown in FIG. 11, the core shaft 10F has a first large-diameter portion 15, a second large-diameter portion 16, a tapered portion 17, and a small-diameter portion 18 in this order from the proximal end side toward the distal end side. The first large-diameter portion 15 corresponds to a largest-outer diameter portion having an outer diameter which is largest in the core shaft 10F and constant. The second large-diameter portion 16 has an outer diameter which is smaller than that of the first large-diameter portion 15, and constant. The tapered portion 17 and the small-diameter portion 18 are configured as in the tapered portion 12 and the small-diameter portion 13 according to the first embodiment. Further, the sparsely wound portion 22 of the coil body 20F is disposed at a position to cover the second large-diameter portion 16 instead of the first large-diameter portion 15 of the largest-outer diameter portion.

Even this configuration can relieve coil squeezing due to curvature by virtue of the sparsely wound portion 22. This can also relieve pulling of the core shaft 10F in the axis direction due to contact of the coil body 20F with the core shaft 10F when curved. Therefore, the guide wire IF according to the seventh embodiment can also prevent a decrease in rotational followability when the guide wire is curved.

Eighth Embodiment

Figure 12:
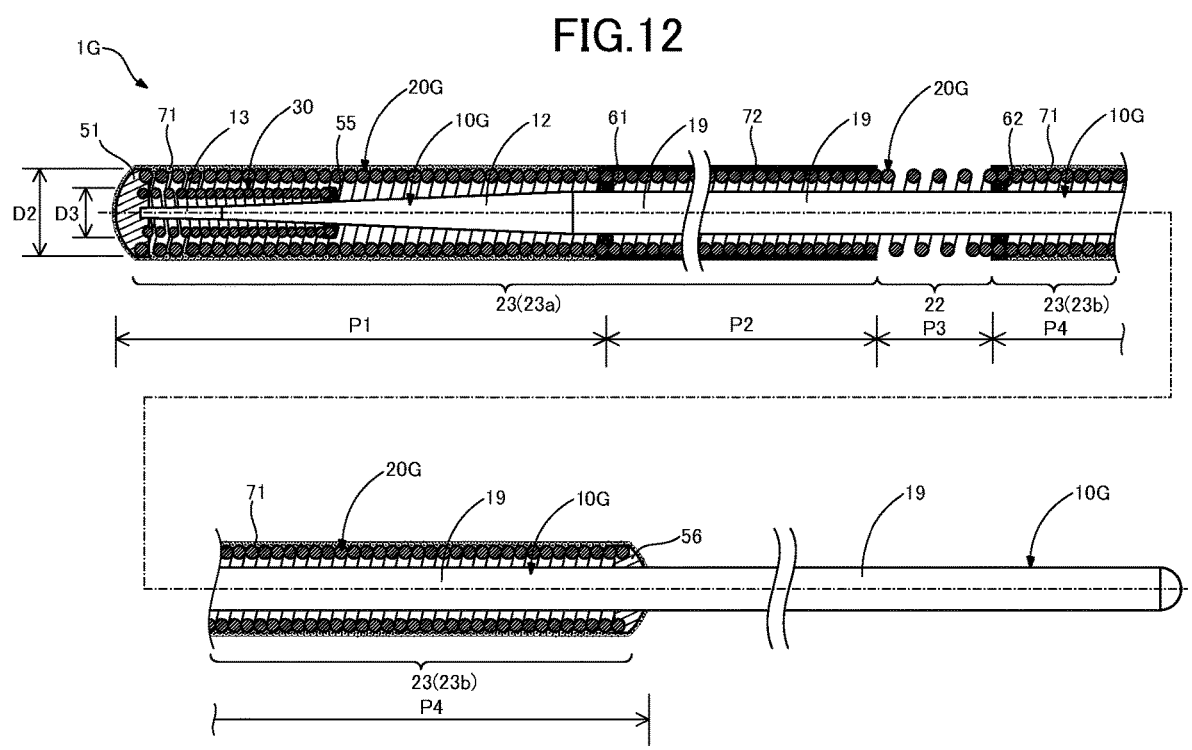
FIG. 12 shows a schematic partial cross-sectional view of the overall configuration of a guide wire according to an eighth embodiment.

FIG. 12 shows a schematic partial cross-sectional view of the overall configuration of a guide wire 1G according to an eighth embodiment. In the guide wire 1 according to the first embodiment, the proximal end of the coil body 20 is connected to the proximal end of the core shaft 10 at the proximal-end joining region 52 (FIG. 1). However, the proximal end of the coil body 20 may be fixed to a portion other than the proximal end of the core shaft 10. For example, the proximal end of the coil body 20G may be fixed in the vicinity of the intermediate portion of the core shaft 10G as in the case of the guide wire 1G according to the eighth embodiment shown in FIG. 12. In this embodiment, the proximal end of the coil body 20G is joined to a large-diameter portion 19 of the core shaft 10G through an intermediate joining region 56. The intermediate joining region 56 can be formed with a similar material as the distal-end joining region 51.

Even this configuration can relieve coil squeezing due to curvature by virtue of the sparsely wound portion 22. This can also relieve pulling of the core shaft 10G in the axis direction due to contact of the coil body 20G with the core shaft 10G when curved. Therefore, the guide wire 1G according to the eighth embodiment can also prevent a decrease in rotational followability when the guide wire is curved.

Ninth Embodiment

Figure 13:
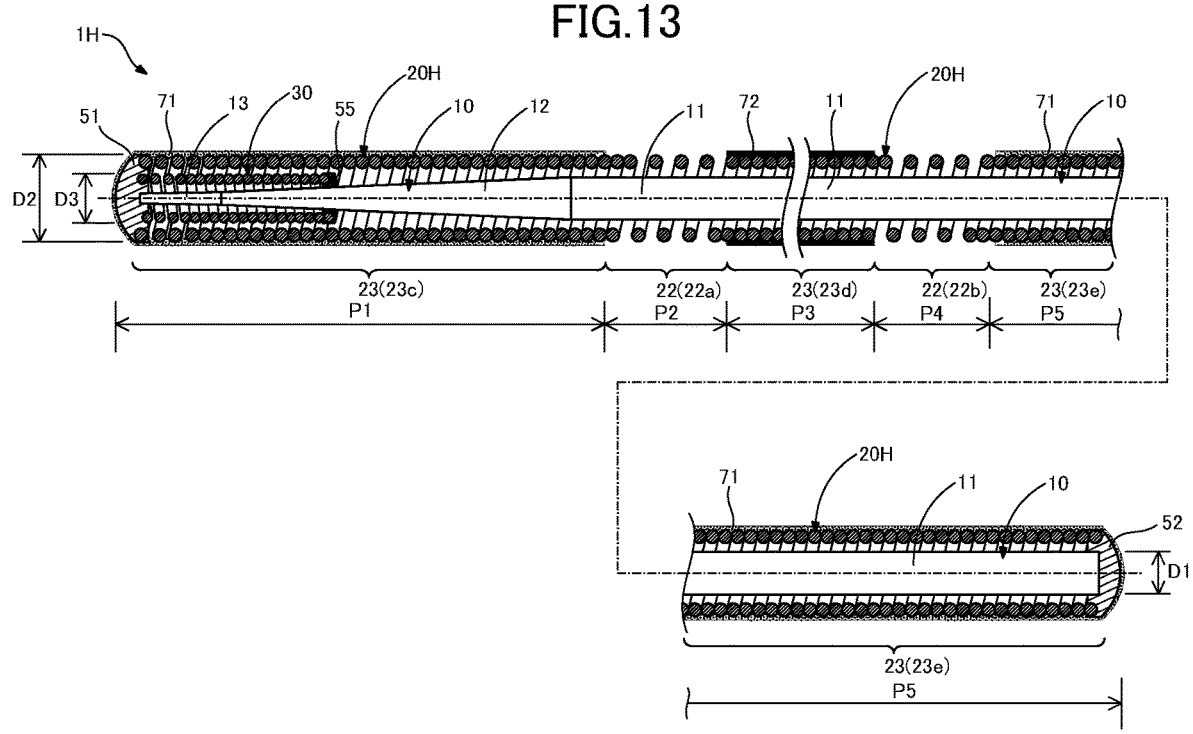
FIG. 13 shows a schematic partial cross-sectional view of the overall configuration of a guide wire according to a ninth embodiment.

FIG. 13 shows a schematic partial cross-sectional view of the overall configuration of a guide wire 1H according to a ninth embodiment. The guide wire 1 according to the first embodiment includes two intermediate fixing portions (the first intermediate fixing portion 61, the second intermediate fixing portion 62) (FIG. 1). However, the number of intermediate fixing portions may be different from the above. For example, an intermediate fixing portion may be omitted as in the case of the guide wire 1H according to the eighth embodiment shown in FIG. 13. Even this configuration can relieve coil squeezing due to curvature by virtue of a space between turns of a coil of at the sparsely wound portions 22 (the first sparsely wound portion 22a, the second sparsely wound portion 22b). Further, the two sparsely wound portions 22 can relieve pulling of the core shaft 10 in the axis direction due to contact of the coil body 20H with the core shaft 10 when curve. Therefore, the guide wire 1H according to the ninth embodiment can also prevent a decrease in rotational followability when the guide wire is curved. It is noted that three or more intermediate fixing portions may be formed, or one intermediate fixing portion may be formed. The width, size, and mode of fixing may be different from the above.

Variations of Present Embodiments

The present disclosure shall not be limited to the above embodiments, but can be implemented according to various aspects without departing from the scope and spirit of the present disclosure. For example, the following variations may be possible.

Variation 1

In the guide wires 1, 1A to 1H according to the first to ninth embodiments, a resin coating (the first resin coating 71 or the second resin coating 72) is formed in at least a portion of the outer surfaces of the coil bodies 20, 20A to 20H. However, the outer surface of a coil body of a guide wire may be entirely exposed without being covered with a resin coating at all. Further, at least a portion of the outer surface of the coil body 20 in a guide wire may be covered with a non-resin coating such as a metal coating. In the guide wires according to any one of the first to ninth embodiments, a resin coating is not formed at the sparsely wound portion 22. However, a resin coating may be formed in at least a portion of the sparsely wound portion 22. Further, a resin coating formed on the outer surface of the coil body does not need to be interrupted at the sparsely wound portion 22, but a resin coating may be continuously formed throughout the sparsely wound portion 22 and the closely wound portions 23. It is noted that no resin coating is preferably formed at the sparsely wound portion 22.

Variation 2

In the guide wire 1 according to the first embodiment, the sparsely wound portions 22 may be disposed in both the coil body 20 and the inner coil body 30 at the same location. This configuration can facilitate to curvature when the distal end of the guide wire 1 is curved and deformed, leading to improved plastic deformability.

Variation 3

In the guide wire 1 according to the first embodiment, the outer diameter D2 of the coil body 20 does not need to be constant. Further, the outer diameter D3 of the inner coil body 30 in the guide wire 1 does not need to be constant. Moreover, the outer diameter D1 of the large-diameter portion 11 of the core shaft 10 does not need to be constant.

Variation 4

In the guide wire 1 according to the first embodiment, the closely wound portion 23 may be formed only at one side of the sparsely wound portion 22 instead of the both sides. That is, the sparsely wound portion 22 may be formed at the distal end or the proximal end of the coil body 20. It is noted that the sparsely wound portion 22 is preferably disposed in the vicinity of the middle of the coil body 20, and the closely wound portions 23 are preferably formed at the both sides.

Variation 5

In the guide wire 1 according to the first embodiment, the sparsely wound portion 22 is disposed in the coil body 20 at a position to cover a portion around which the inner coil body 30 of the core shaft 10 is wound. Even this configuration can prevent a decrease in rotational followability of the guide wire due to curvature.

Variation 6

The configurations of the guide wires according to the first to ninth embodiments may be combined in an appropriate manner. For example, a resin coating does not need to be formed on a portion of the outer surface of the guide wire 1A according to the second embodiment (FIG. 6) as in the case of the closely wound portion 23 of the third embodiment (FIG. 7). Alternatively, the inner coil body 30 may, for example, be omitted as in the case of the fifth embodiment (FIG. 9). Alternatively, the guide wire 1C according to the fourth embodiment (FIG. 8) may be entirely covered with a single type of resin coating except for the sparsely wound portion 22 as in the case of the coil body 20E according to the sixth embodiment (FIG. 10).

As described above, the present aspect is described based on the embodiments and variations, but the aforementioned modes of implementing the aspect are provided merely for better understanding of the present aspect, and shall not be construed as limiting the present aspect. Alternations and improvements may be made in the present aspect without departing from the scope and spirit of the claims, and equivalents thereof fall within the scope of the present aspect. Moreover, a technical feature may be omitted, if desired, unless otherwise stated as essential in the present specification.

DESCRIPTION OF THE REFERENCE NUMERALS 1, 1A to 1H Guide wire
10, 10F, 10G Core shaft
11 Large-diameter portion
12 Tapered portion
13 Small-diameter portion
15 First large-diameter portion
16 Second large-diameter portion
17 Tapered portion
18 Small-diameter portion
19 Large-diameter portion
20, 20A to 20H Coil body
22 Sparsely wound portion
23 Closely wound portion
30 Inner coil body
51 Distal-end joining region
52 Proximal-end joining region
55 Inner joining region
56 Intermediate joining region
61 First intermediate fixing portion
62 Second intermediate fixing portion
71 First resin coating
72 Second resin coating
81 Polyethylene tube
84 Guide wire

The invention claimed is:
1. A guide wire, comprising:
a core shaft;
a coil wound around the core shaft;
a distal-end joining region to which a distal end of the core shaft and a distal end of the coil are joined;
a proximal-end joining region to which a proximal end of the core shaft and a proximal end of the coil are joined; and
an inner coil disposed in an inner side of the coil and wound around the core shaft, wherein
the coil has a sparsely wound portion having a sparser coil pitch than other portions of the coil, the sparsely wound portion being disposed between the distal-end joining region and the proximal-end joining region,
the inner coil is shorter in length than the coil, and a distal end of the inner coil is joined to the distal end of the core shaft at the distal-end joining region, and
the sparsely wound portion is disposed in the coil at a position to cover a portion of the core shaft around which the inner coil is not wound.

2. A guide wire, comprising:
a core shaft;
a coil wound around the core shaft;
a distal-end joining region to which a distal end of the core shaft and a distal end of the coil are joined; and
a proximal-end joining region to which a proximal end of the core shaft and a proximal end of the coil are joined, wherein
the coil includes (1) a sparsely wound portion having a sparser coil pitch than other portions of the coil, the sparsely wound portion being disposed between the distal-end joining region and the proximal-end joining region, (2) a first closely wound portion having a closer coil pitch than the sparsely wound portion, the first closely wound portion being disposed at a distal end side relative to a distal end of the sparsely wound portion, and (3) a second closely wound portion having a closer coil pitch than the sparsely wound portion, the second closely wound portion being disposed at a proximal end side relative to a proximal end of the sparsely wound portion,
a first resin coating is formed on an outer surface of the first closely wound portion,
a second resin coating is formed on an outer surface of the second closely wound portion,
the first resin coating and the second resin coating are separated by the sparsely wound portion,
each of the first resin coating and the second resin coating includes a hydrophobic resin part, the hydrophobic resin part being a longitudinal section that is hydrophobic, and
the first resin coating further includes a hydrophilic resin part having a hydrophilic group, the hydrophilic resin part being another longitudinal section disposed on a more proximal end side of the guide wire than the hydrophobic resin part of the first resin coating.

3. The guide wire according to claim 2, wherein the hydrophilic resin part has better lubricity than the hydrophobic resin part.

4. A guide wire, comprising:
a core shaft;
a coil wound around the core shaft;
a distal-end joining region to which a distal end of the core shaft and a distal end of the coil are joined; and
a proximal-end joining region to which a proximal end of the core shaft and a proximal end of the coil are joined, wherein
the coil includes (1) a sparsely wound portion having a sparser coil pitch than other portions of the coil, the sparsely wound portion being disposed between the distal-end joining region and the proximal-end joining region, (2) a first closely wound portion having a closer coil pitch than the sparsely wound portion, the first closely wound portion being disposed at a distal end side relative to a distal end of the sparsely wound portion, and (3) a second closely wound portion having a closer coil pitch than the sparsely wound portion, the second closely wound portion being disposed at a proximal end side relative to a proximal end of the sparsely wound portion,
a first resin coating is formed on an outer surface of a portion of the first closely wound portion in a predetermined range from the distal end of the first closely wound portion,
a second resin coating is formed on an outer surface of the second closely wound portion,
the first resin coating and the second resin coating are separated by the sparsely wound portion and a proximal end side part of the first closely wound portion, each of the first resin coating and the second resin coating includes a hydrophobic resin part, the hydrophobic resin part being a longitudinal section that is hydrophobic, and the first resin coating further includes a hydrophilic resin part having a hydrophilic group, the hydrophilic resin part being another longitudinal section disposed on a more proximal end side of the guide wire than the hydrophobic resin part of the first resin coating.

5. The guide wire according to claim 4, wherein the hydrophilic resin part has better lubricity than the hydrophobic resin part.

* * * * *